United States Patent [19]

Elias et al.

[11] 4,392,850
[45] Jul. 12, 1983

[54] IN-LINE TRANSFER UNIT

[75] Inventors: Allen M. Elias, Mundelein; Joseph N. Genese, Waukegan, both of Ill.

[73] Assignee: Abbott Laboratories, North Chicago, Ill.

[21] Appl. No.: 324,194

[22] Filed: Nov. 23, 1981

[51] Int. Cl.³ .............................................. A61J 1/00
[52] U.S. Cl. ...................................... 604/82; 604/88; 604/244; 604/413; 604/414; 604/416
[58] Field of Search ................... 604/82, 83, 84, 85, 604/86, 87, 88, 244, 251, 252, 255, 262, 403, 405, 408, 411, 413, 414, 415, 416, 56, 246; 141/329, 330

[56] References Cited

U.S. PATENT DOCUMENTS

| | | | |
|---|---|---|---|
| 1,630,248 | 5/1927 | Aguilar | 604/7 |
| 2,682,268 | 6/1954 | Ryan et al. | 604/5 |
| 2,702,034 | 2/1955 | Walter | 604/262 |
| 2,954,769 | 10/1960 | Callahan et al. | 128/272 |
| 3,001,525 | 9/1961 | Hendricks | 604/251 X |
| 3,462,361 | 8/1969 | Greenwalt et al. | 604/7 |
| 3,685,795 | 8/1972 | Caster | 604/244 |
| 3,788,369 | 1/1974 | Killinger | 604/408 X |
| 3,788,524 | 1/1974 | Davis et al. | 604/414 X |
| 3,902,489 | 9/1975 | Carter | 604/411 |
| 3,938,520 | 2/1976 | Scislowicz et al. | 128/272.3 |

FOREIGN PATENT DOCUMENTS 1082035  6/1954  France ..................................... 604/88

Primary Examiner—Richard J. Apley
Assistant Examiner—Michelle Lester
Attorney, Agent, or Firm—Neil E. Hamilton; Robert L. Niblack

[57] ABSTRACT

A sterile container for a medicinal material which is to be intermixed in an I.V. solution wherein the container serves as a mixing device as well as a portion of an I.V. administration apparatus. The device of this invention includes a container which is closed at opposing ends by pierceable diaphragm portions. Extending from one end is a piercing pin having a diaphragm piercing portion which can pierce the diaphragm when it is moved inwardly into the container and also provide a fluid passageway for the container contents. At the opposing end a diaphragm is housed in a closure with a flexible end wall and a tubular guide section for the piercing pin of an I.V. administration set. The container therefore serves a dual function of holding a fluid material such as a powder in a sterile condition yet serving as a component of an I.V. set to thereby afford a quick and simple procedure for mixing additive components into an I.V. administration set.

16 Claims, 6 Drawing Figures

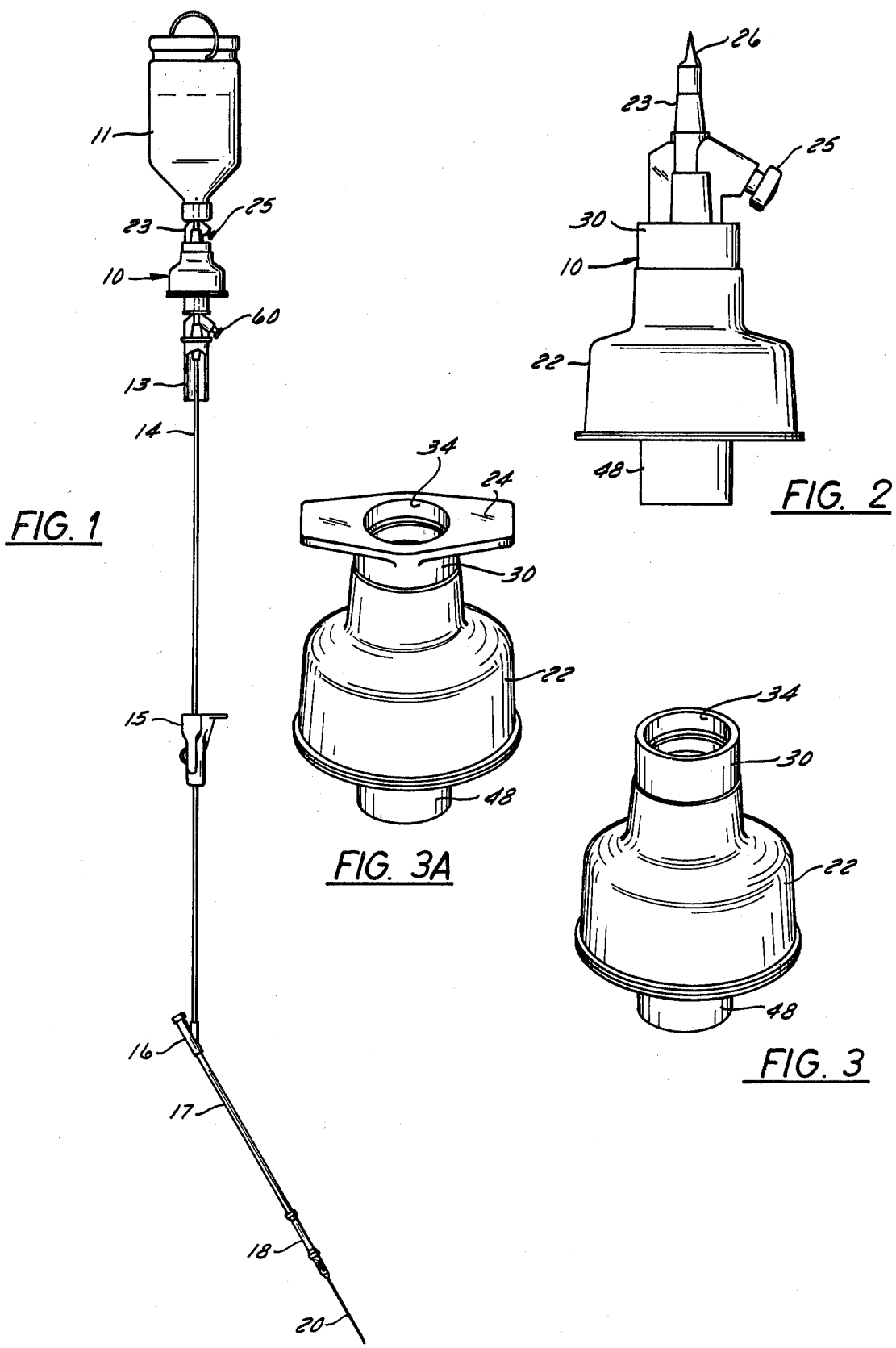

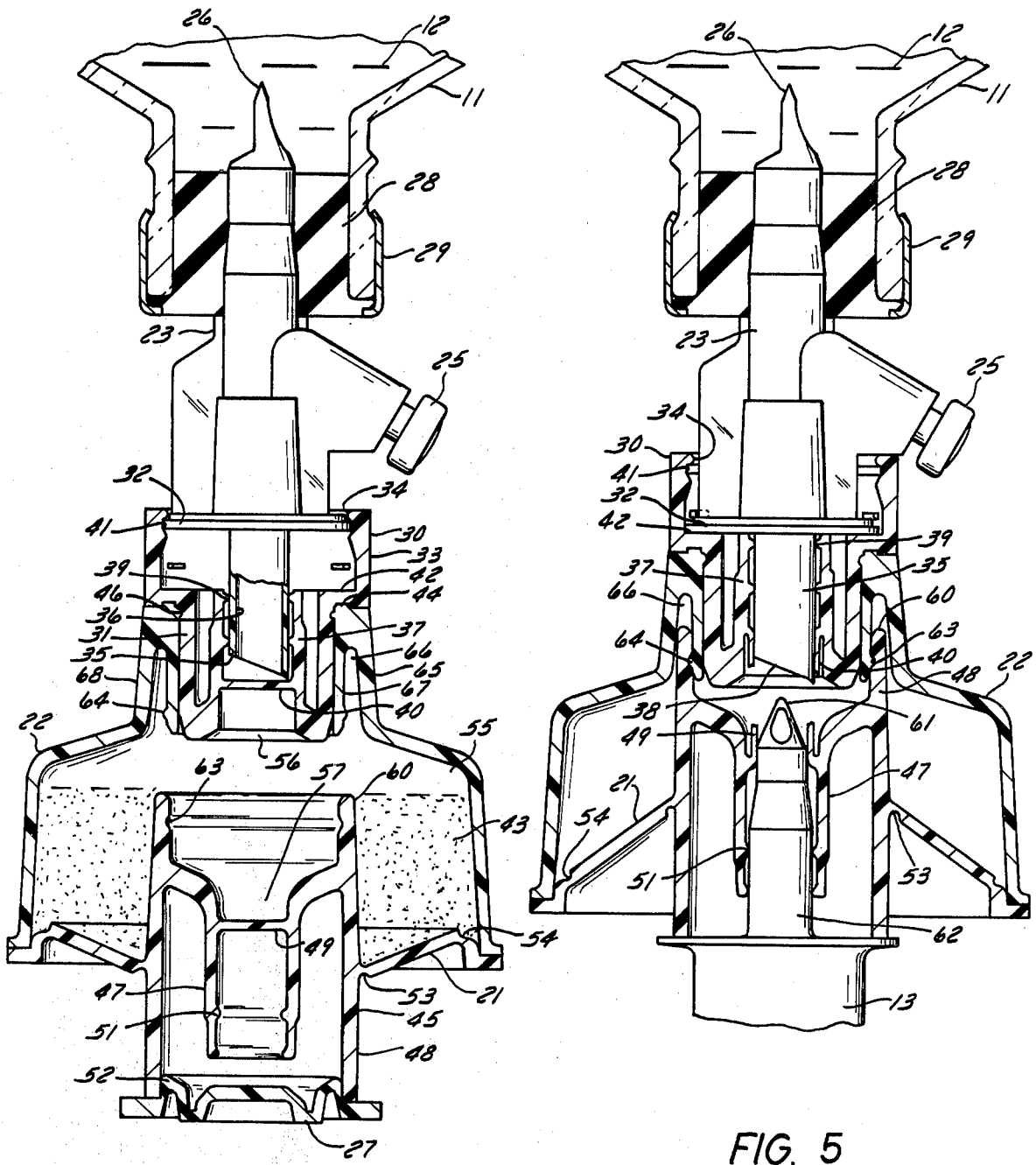

IN-LINE TRANSFER UNIT

BACKGROUND OF THE INVENTION

This invention relates to an additive container for use in admixing materials into an I.V. solution administration device. More particularly, this invention relates to an additive container for admixing I.V. solutions which not only facilitates the admixing of the additive material such as a powder into the I.V. solution but also serves as an integral part of the I.V. administration set.

In U.S. Pat. No. 3,001,525, an additive-type container is disclosed which is subsequently interconnected into an I.V. administration apparatus after the contents are admixed therewith. The problem with this particular container system is that the maintenance of sterility can be a problem due to the fact that a cap portion must be removed for subsequent connection with an I.V. set. Further, caps which are utilized to maintain sterility can inadvertently become detached and thus impair the sterility of the product. The usual additive type transfer apparatus are disclosed in U.S. Pat. Nos. 2,954,769 as well as 3,938,520 and RE29,656. In U.S. Pat. Nos. 1,630,248; 2,682,268; 2,702,034 and 3,462,361 various types of I.V. in-line containers without drugs are disclosed. In U.S. Pat. Nos. 3,685,795; 3,902,489 and 4,080,965 various types of in-line piercing devices are illustrated. The prior art does not describe an additive container device which can assure the sterility of the product prior to its being intermixed with an I.V. solution, provide a positive pumping action for mixing purposes as well as forming a component part of the I.V. administration apparatus for ease of administering the resulting solution.

It is an advantage of the present invention to afford a container for sterile material which will maintain the sterility of the material yet afford a quick and efficient means of transferring the material into an I.V. solution. Other advantages are a sterile transfer unit which in the case of the I.V. solution being in the bottle will provide a venting therefor; a transfer unit which affords a sterile interconnecting means with an I.V. administration set; a transfer container member which can be easily fabricated from plastic materials in an economical manner and thus is disposable; and a transfer device which affords a positive pumping action for mixing the additive material with the sterile I.V. liquid.

SUMMARY OF THE INVENTION

The foregoing advantages are accomplished and the shortcomings of the prior art are overcome by the present in-line transfer unit which contains a powder material and is readily adaptable to be connected to a first container with I.V. liquid such as a liquid solution with the contents of both containers to be subsequently delivered through the second or transfer container. The transfer container has opposing passageways sealed by closures for storing the fluid material to be transferred. First and second closures provide in part pierceable diaphragm portions. A transfer member has a passageway therethrough with a piercing end on one end and a diaphragm piercing portion on the other end. Retentive movement means are provided with the first closure and the transfer member to permit sufficient movement of the transfer member so that the piercing portion thereof can pierce the diaphragm of the first closure. A flexible end wall is disposed in the second container integrally connected to the guide member having the diaphragm. When the piercing end of the transfer member is in fluid communication with the solution container, the diaphragm piercing portion can be moved to pierce the diaphragm portion of the second container and permit in part the intermixing of the material therein with the contents of the transfer container by an inward movement of the flexible end wall. Subsequently, the opposing diaphragm portion of the second closure can be pierced by another piercing member of an I.V. set and the contents of both containers will flow through and out of the second container by means of the piercing member of the I.V. set. In a preferred manner the closure sealing the passageways in the containers include guide members for the piercing members with the diaphragm portions placed inwardly therein. Also preferably the first closure is formed separately from the transfer container and the second closure is formed integrally therewith. The first closure includes an inner cavity section for frictionally receiving a portion of the guide member in the second closure. The container is fabricated from a cylindrical flexible wall member and will have attached a piercing member in slidable engagement at one end and a closure cap secured at the opposing end.

DESCRIPTION OF THE DRAWINGS

A better understanding of the present in-line transfer unit will be had by reference to the drawings wherein:

FIG. 1 is a view in side elevation showing the in-line transfer unit integrally connected in an I.V. administration set.

FIG. 2 is a view in side elevation showing the in-line transfer unit as it would be initially packaged with a sterile powdered material and prior to use.

FIG. 3 is a perspective view of the in-line transfer unit immediately after filling with a medicinal material.

FIG. 3A is a perspective view of an alternative embodiment.

FIG. 4 is a view in partial vertical section showing the in-line transfer container as it is initially placed in fluid communication with an I.V. solution container.

FIG. 5 is a view similar to FIG. 4 except showing the in-line transfer unit in fluid communication with the I.V. solution container as well as an I.V. administration set.

DESCRIPTION OF ONE EMBODIMENT

Proceeding to a detailed description of the present invention, the in-line transfer unit generally 10 is shown in FIG. 1 in fluid communication with an I.V. liquid container 11 and a vented piercing pin 13 at the opposite end. The usual length of flexible tubing 14 extends from the piercing pin 13 to a Y reseal unit 16. A flow control clamp 15 is placed therebetween. Extending from the Y reseal unit 16 is the usual additional length of tubing 17 interconnected to a needle adapter 18 with the hypodermic needle 20 attached thereto. As best seen in FIG. 2, the in-line transfer unit 10 has a vented piercing pin 23 secured at one end in closure portion 30. Vented piercing pin 23 has the usual piercing tip 26 and the lateral air vent 25 with piercing pin 23 being slidably received in closure portion 30. An additional annular wall portion 48 in part seals the opposite end of the container 22 forming a part of the in-line transfer unit 10.

As best seen in FIG. 4, container 22 is closed at the top by means of closure member 30 having a wall portion 31 for sealing inside container 22. Closure member 30 includes an enlarged portion 33 for housing in a slidable manner, flange 32 of piercing pin 23. An internal flange 34 is provided at the end thereof to provide a stop for flange 32. A central tubular guide section 37 is integrally connected with wall portion 31 and provides ribs such as 39 for frictional contact with tubular portion 35 of piercing pin 23. A diaphragm 40 extends across tubular guide section 37 and is designed to be pierced by beveled piercing portion 38 of vented piercing pin 23. Additional securing of closure member 30 to container 22 is afforded by means of raised portions such as 44 and 46 extending from container 22 into accommodating grooves in the closure 30.

The opposite end of container 22 is closed by closure section 45 which like closure 30 has a tubular guide section 47 also having a diaphragm 49 and ribs 51 for subsequent contact with the piercing spike such as 62 for piercing of the diaphragm 49. Closure cap 27 is retained on wall portion 48 extending outwardly from guide section 47 of closure section 45 by means of flexible wall 52 on cap 27. It will be noted that closure section 45 is hingedly attached to container 22 by a flexible end wall portion 21. The flexing is afforded through weakened portions 53 and 54. A compartment 66 is provided between outer wall 65 and inner wall 67 of end closure portion 68 to receive a section 60 of wall portion 48. Frictional engagement and an interlock is afforded by flange 64 and groove 63. It will be noted that closures 30 and 45 seal passageways such as 56 and 57 in container 22 which but for the closures would permit the flow of powdered or liquid material 43 therefrom.

Operation

A better understanding of the advantages of the in-line transfer unit will be had by a description of its operation. The in-line transfer unit will be filled with the powdered or liquid material 43 from the open top thereof with closure portion 30 having been removed. After filling, closure 30 will be placed on container 22 as shown in FIG. 3. Vented piercing pin 23 will next be placed in closure portion 30 to result in the unit 10 which will be packaged and appear as in FIG. 2 prior to use. It will contain a sterile powdered material 43 such as a freeze dried antibiotic. In a preferred manner, the container 22 will be molded from a flexible plastic material such as polyethylene with closure section 45 integrally molded therewith having diaphragm 49. This will form a complete closure for the normal passageway 57 at one end thereof. A cap 27 will be placed thereon to further protect the sterility of tubular guide section 47. Under sterile conditions, closure member 30 will be placed on the opposing end portion 68 and flange 32 of piercing pin 23 will be force fitted over flange 34 to rest in groove 41. This will place piercing portion 38 away from diaphragm 40. The usual protective cap will be placed over piercing point 26. When it is desired to intermix material 43 with liquid 12, all that is required is for piercing point 26 to be inserted through sealing plug 28 retained in container 11 by ferrule 29, as indicated in FIG. 4. After insertion, container 22 will be moved in the direction of the piercing pin which will cause flange 32 to ride out of groove 41 until it bottoms on floor surface 42 as indicated in FIG. 5. In this position, as shown in FIG. 5, piercing portion 38 will have pierced through diaphragm 40 to effect fluid communication between container 11 and container 22 through passage 36 in tubular portion 35. To assist in the intermixing of the material 43 with the liquid 12, the flexible wall 21 of container 22 can be moved inwardly and outwardly to effect a pumping action. This will result in a solution being formed from liquid 12 and material 43 in cavity 55. To also aid in the intermixing of solution 12 and material 43, bottle 11 and container 22 are inverted so that all the fluid escapes chamber 55. After the desired intermixing, and while bottle 11 and container 22 are inverted, cap 27 will be removed and spike 62 of piercing pin 13 inserted into tubular guide 47 so that piercing point 61 will pierce through diaphragm 49 of closure section 45. This movement will advance cylindrical portion 60 until groove 63 and rib 64 interlock thereby isolating chamber 55 from fluid pathway 56. In this condition, the in-line container 10 will be in the position shown in FIGS. 1 and 5 and form a portion of the I.V. administration set. The set will then be utilized in the normal manner with the venipuncture being made by means of needle 20.

In FIG. 3A an alternative embodiment of container 22 is illustrated. A finger engagement flange 24 extends transversely from closure portion 30. This acts as a grip-push surface that can be used to cause the piercing pin 23 to cut through container sealing plug 28. Having such a flange avoids having to push on the undersurface of container 22, thereby eliminating the risk of accidental manipulation of flexible member 21.

As indicated earlier, the preferred material for fabricating container 22 is polyethylene. However, other semiflexible materials which will not contaminate sterile materials can be utilized such as ethylene-vinyl acetate copolymer, polypropylene or polybutylene. The piercing pin units 23 and 13 are of the standard type and are composed of an acrylonitrile butadiene styrene plastic material. It should be pointed out that in addition to providing liquid passage they provide independent passage for air from the air vents 25 and 60, up to the end of piercing points such as 26 and 61. In the instance where a flexible container is to be utilized, it would not be necessary to have an air venting and this could be eliminated or the air vent secluded from outside atmosphere. While the in-line container is designed to be used in conjunction with the powdered material, it will be readily appreciated that liquids could be readily employed. Further, while closure 45 is shown as being integrally formed with container 22, it could be formed as a separate part.

It will thus be seen that through the present invention there is now provided an in-line additive container which affords a sterile condition for the additive material yet can be readily interconnected into an I.V. set for ease of administration. Another benefit of the disclosed system is that medications may be stored in a stable, risk free, contamination free state immediately adjacent to the in use location within the hospital. Therefore, as the medication is needed by the patient, the attending nurse, at the patient's bedside, may easily, quickly and with minimal risk of contamination, prepare the medication and administer in an extremely brief period of time. This is favorable over having the medication mixed in the pharmacy which may be at some distance from the patient's bedside, and have to be transported to the patient in need. Also, should it be necessary to administer two compatible medications, two series devices 10, each containing a distinct medication, may be assembled in tandem to permit immediate reconstitution of the drugs and administration of the drugs within a matter of minutes. The in-line container can be fabricated from conventional component parts. It therefore will not appreciably add to the cost of an I.V. administration. Most importantly, the unit is not susceptible to being accidentally contaminated prior to use and is designed to prevent contamination as well as aid in the mixing of the powder and liquid during its use through the novel pumping feature.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. An in-line transfer unit for mixing a sterile fluid material from a first container into a second container with the contents of both containers to be subsequently delivered through said second container, said unit comprising;
   a container having opposing passageways for storing a fluid material to be transferred;
   first and second closures sealing the passageways in said container, said closures defined in part by pierceable diaphragm portions;
   a transfer member having a passage therethrough with a piercing end on one end and a diaphragm piercing portion on the other end;
   retentive movement means operatively associated with said first closure and said transfer member to permit sufficient movement of said transfer member so that said piercing portion thereof can pierce said diaphragm of said first closure; and
   a flexible end wall defining a portion of said second closure;
   so that when the piercing end of the transfer member is in fluid communication with said first container, said diaphragm piercing portion can be moved to pierce said diaphragm portion of said second container and permit in part the intermixing of the material therein with the contents of said first container by an inward movement of said flexible end wall, and subsequently, the opposing diaphragm portion of said second closure will be pierced by another piercing member and the contents of both containers will flow through and out of said second container by means of said other piercing member.

2. The in-line transfer unit as defined in claim 1 wherein said closures sealing the passageways in the containers are defined by guide members for said transfer member and said other piercing member with said diaphragm portions placed inwardly therein.

3. The in-line transfer unit as defined in claim 2 wherein said flexible end wall is integrally connected to said guide member in said second closure.

4. The in-line transfer unit as defined in claim 3 wherein said first closure includes a closure portion defining an inner cavity means for frictionally receiving a portion of said guide member of said second closure and thereby providing an interlock therebetween.

5. The in-line transfer unit as defined in claim 2 wherein said second closure is defined by a wall portion extending outwardly and spaced from said guide member, said wall portion providing securing means to receive a removable cap member.

6. The in-line transfer unit as defined in claim 5 wherein said first closure includes an outwardly extending wall portion and spaced from said guide member, said wall portion defining said retentive movement means for said associated transfer member.

7. The in-line transfer unit as defined in claim 6 wherein said transfer member associated with said first closure includes means integrally associated therewith to vent said first container when said transfer member is in fluid communication therewith.

8. The in-line transfer device as defined in claim 5 wherein said first closure is formed separately from said container and said second closure is formed integrally therewith.

9. The in-line transfer device as defined in claim 8 wherein said container is formed in part from a flexible wall member.

10. The in-line transfer device as defined in claim 2 wherein said guide members are defined by tubular members and include internal frictional engagement ribs for contact with said transfer member and said other piercing member.

11. The in-line transfer device as defined in claim 2 wherein said other piercing member comprises a portion of an intravenous solution administration set.

12. A container for the sterile fluid material which can be later interconnected into an intravenous solution administration set including a solution container to administer the fluid material thereby, comprising:
    a substantially cylindrical container having opposing openings for storing a fluid material to be transferred;
    first and second closures sealing the openings in said container, said closures defined in part by tubular guide members integrally formed with pierceable diaphragm portions with said second closure further including a flexible end wall integrally connected to said guide member;
    a transfer member in the form of a channeled piercing pin having a diaphragm piercing portion at one end; and
    means operatively associated with said first closure and said transfer member to permit movement of said transfer member so that said diaphragm piercing portion can pierce said diaphragm portion of said cylindrical container and permit in part intermixing of the fluid material therein with the contents of said solution container by an inward movement of said flexible end wall, and subsequently, the opposing diaphragm portion of said second closure will be pierced by another piercing pin member and the contents of both containers will be administered by said administration set.

13. The container for a sterile fluid material as defined in claim 12 wherein said fluid material is a sterile powder and said flexible end wall is finger pressible.

14. The container for a sterile fluid material as defined in claim 13 wherein said pierceable diaphragm portions are positioned within the confines of said cylindrical container.

15. The container for a sterile fluid material as defined in claim 14 wherein at least one of said closures is integrally formed with said cylindrical container.

16. The container for a sterile fluid material as defined in claim 14 wherein at least one of said piercing pins includes integral venting means.

* * * * *